US00PP20765P2

(12) United States Plant Patent
Ranney

(10) Patent No.: US PP20,765 P2
(45) Date of Patent: Feb. 16, 2010

(54) ***HYDRANGEA* PLANT NAMED 'NCHA1'**

(50) Latin Name: *Hydrangea arborescens*
Varietal Denomination: NCHA1

(75) Inventor: Thomas G. Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/313,080

(22) Filed: Nov. 17, 2008

(51) Int. Cl.
*A01H 5/00* (2006.01)

(52) U.S. Cl. ..... Plt./250

(58) Field of Classification Search ..... Plt./250
See application file for complete search history.

(56) References Cited

OTHER PUBLICATIONS

GTITM UPOVROM Citation for 'NCSUHA1' as per CA PBR 08-6471, filed Nov. 28, 2008.*

* cited by examiner

*Primary Examiner*—Kent L Bell
(74) *Attorney, Agent, or Firm*—Jondle & Associates, P.C.

(57) ABSTRACT

'NCHA1' is a new *Hydrangea* plant particularly distinguished by having a medium-sized, rounded, multi-stemmed shrub, a unique combination of compound, corymb inflorescences with prevalent sterile flowers and rose to pink colored sepals, is disclosed.

2 Drawing Sheets

Genus and species: *Hydrangea arborescens*.

Variety denomination: 'NCHA1'.

BACKGROUND OF THE INVENTION

The present invention comprises a new and distinct cultivar of *Hydrangea*, botanically known as *Hydrangea arborescens*, and hereinafter referred to by the cultivar name 'NCHA1'. This new *Hydrangea* was developed through a breeding program at Mills River, N.C. 'NCHA1' originated as an open pollinated (F2) seedling from *H. arborescens* cultivar 'H2005-045-061' (unpatented) that was grouped in an isolation block with full sibling plants of the same parentage.

The first asexual propagation of 'NCHA1' was carried out in June 2006 by rooting stem cuttings at Mills River, N.C., USA and has been asexually reproduced repeatedly by vegetative cuttings in North Carolina over a two year period. 'NCHA1' roots readily from softwood cuttings treated with a basal dip of 2,500–4,000 ppm indole butyric acid (potassium salt) in water. 'NCHA1' has been found to retain its distinctive characteristics through successive asexual propagations.

Plant Breeder's Rights for this cultivar have been applied for. 'NCHA1' has not been made publicly available more than one year prior to the filing of this application.

SUMMARY OF THE INVENTION

The following are the most outstanding and distinguishing characteristics of this new cultivar when grown under normal horticultural practices at Mills River, N.C., USA.

1. Medium-sized, rounded, multi-stemmed shrub;
2. Rose to pink colored sepals; and 3. Compound, corymb inflorescences with prevalent sterile flowers.

DESCRIPTION OF THE PHOTOGRAPHS

This new *Hydrangea* plant is illustrated by the accompanying photographs which show the plant's form, foliage and inflorescences. The colors shown are as true as can be reasonably obtained by conventional photographic procedures. The photographs were taken on 2-year-old plants in July 2008, growing under landscape conditions in Arden, N.C.

DESCRIPTION OF THE NEW CULTIVAR

Figure 1:
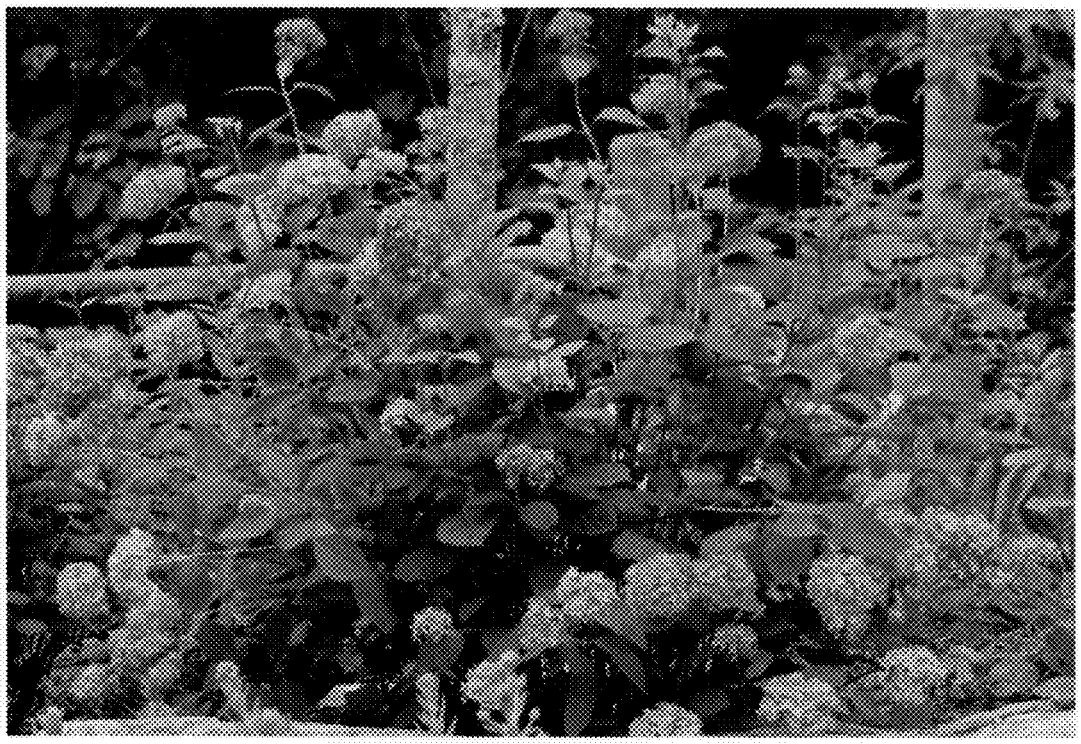
FIG. 1 Shows the mature plant habit.
Figure 2:
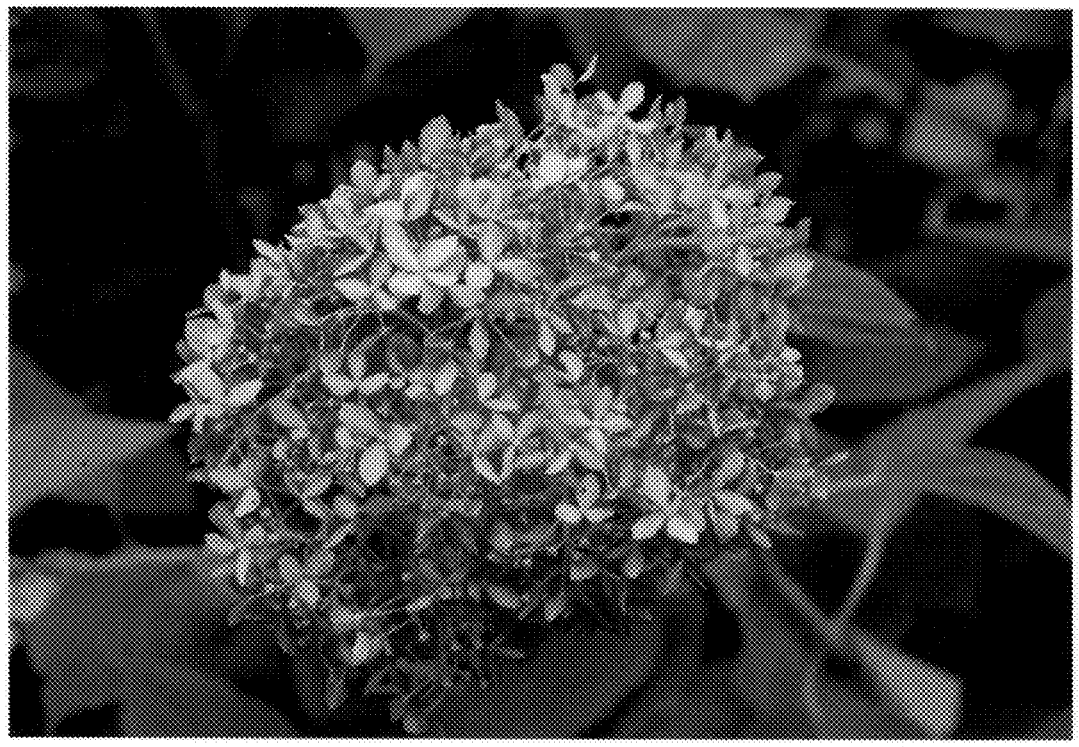
FIG. 2 Shows a close-up of the mature inflorescences.
Figure 3:
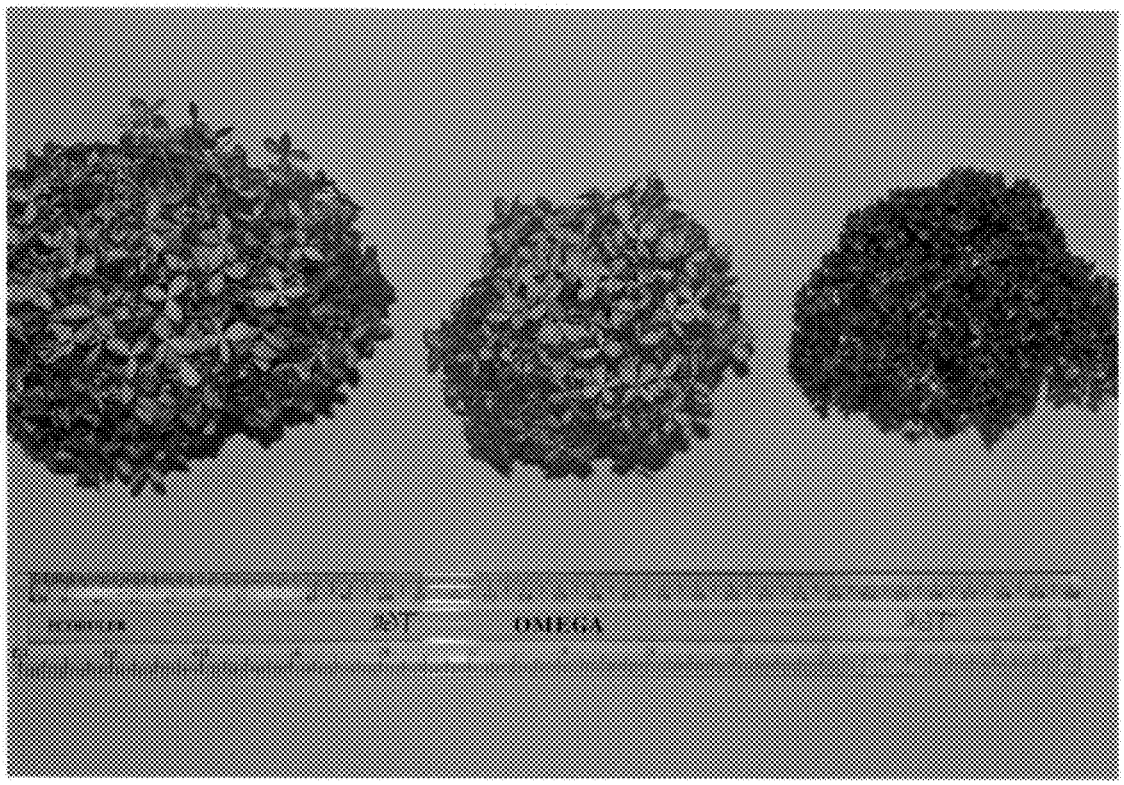
FIG. 3 Shows the size and color ranges of mature inflorescences.

The following detailed description sets forth the distinctive characteristics of 'NCHA1'. The detailed description was taken on 2-year-old plants growing under landscape conditions in Arden, N.C., in July 2008. Color references are to The R.H.S. Colour Chart of The Royal Horticultural Society of London (R.H.S.), 2001 Edition.

DETAILED BOTANICAL DESCRIPTION

Classification:

*Botanical name.*—*Hydrangea arborescens.*

*Common name.*—Smooth *Hydrangea.*

Parentage: 'NCHA1' originated as an open pollinated (F2) seedling from *H. arborescens* cultivar 'H2005-045-061' (unpatented) that was grouped in an isolation block with full sibling plants of the same parentage ('Eco Pink Puff' (unpatented)×'H2004-006-012' (unpatented)).

Plant description:

*Classification.*—Shrub.

*Type.*—Deciduous.

*Form*.—Multi-stemmed.
*Shape*.—Rounded plant habit.
*Usage*.—Adaptable landscape shrub.
*Height* (*from top of soil including inflorescences*).—About 100 cm.
*Diameter* (*including inflorescences*).—About 100 cm.
*Branching habit*.—Freely branching with as many as 100 or more terminal shoots per plant.
*Shoots*.—Length: 50 cm to 100 cm Diameter: 0.3 cm to 1.0 cm Internode length: 5 cm to 15 cm Texture: Glabrous Color: RHS 146C.
*Time to produce a finished plant having inflorescences*.—3 months to 6 months.
*Time to initiate and develop roots*.—3 weeks to 4 weeks.

Leaves:
*Form*.—Simple.
*Arrangement*.—Opposite.
*Number*.—10 to 25 leaves per shoot.
*Length*.—6 cm to 10 cm.
*Width*.—5 cm to 8 cm.
*Shape*.—Broadly ovate.
*Apex*.—Acuminate.
*Base*.—Cordate to rounded
*Margin*.—Dentate to serrate.
*Venation pattern*.—Pinnate, opposite to sub-opposite.
*Venation color* (*both surfaces*).—RHS 191 B.
*Texture*.—Upper surface: Glabrous Lower surface: Slightly pubescent.
*Immature leaf color in summer*.—Upper surface: RHS 138A Lower surface: RHS 138B.
*Mature leaf color in summer*.—Upper surface: RHS 139A Lower surface: RHS 138A.
*Petioles*.—Length: 1.5 cm to 4 cm Diameter: 0.2 cm Color: Upper surface: RHS 181B Lower surface: RHS 146C.

Inflorescence:
*Appearance or form*.—Fertile (approximately 600) and sterile flowers (approximately 600) arranged on individual hemispherical or dome-shaped terminal, compound corymbs.
*Corymb*.—Diameter: 8 cm to 20 cm Height: 5 cm to 12 cm Season: Continuously flowering from late May to early August in Arden, N.C. Quantity: Often 100 or more corymbs per plant over the summer Longevity: Individual corymbs are showy for approximately 4 weeks.
*Sterile flowers*.—Petals, pistils, and stamens are greatly reduced (<0.5 mm) and insignificant Buds: Shape: Round Diameter: 0.1 cm to 0.2 cm Color: RHS 187C Sepals: Number: 2 to 4 Length: 0.5 cm to 0.7 cm Width: 0.3 cm to 0.5 cm Shape: Lanceolate to oval Apex: Acute Base: Attenuate Margin: Entire Texture: Smooth/glabrous Color (when expanding, both surfaces): RHS 187C Color (when fully expanded, both surfaces): Ranges from RHS 68D to RHS 68C, and from RHS N66D to RHS N66C.
*Fertile flowers*.—Sepals and petals are greatly reduced (<0.5 mm) and insignificant Buds: Shape: Round Diameter: 0.1 cm to 0.2 cm Color: RHS 186B Flower size: Width: 0.1 cm to 0.2 cm Height: 0.2 cm to 0.3 cm.

Reproductive organs:
*Pistils*.—2, fused Color: RHS 155B throughout Length: 0.2 cm Stigma: Blunt Stigma diameter: 0.025 cm Style length: 0.1 cm Ovary shape: Rounded Ovary diameter: 0.1 cm.
*Stamens*.—Number: 10 Anther: Shape: Rounded, fusiform Length: 0.025 cm long Color: RHS 158D Filament length: 0.2 cm Filament color: RHS 155B Pollen: Scarce.

Fruit/seed set: Seeds are minute, dust-like.
Disease and insect resistance: No significant disease or insect pests have been observed.

COMPARISON WITH PARENTAL LINES AND KNOWN CULTIVAR

'NCHA1' is distinguished from cultivar 'H2005-045-061' by having a compound, corymb inflorescence with prevalent sterile florets.

'NCHA1' has a unique combination of compound, corymb inflorescences with around 600 prevalent sterile flowers and rose to pink colored sepals not found in other known commercial cultivars of *Hydrangea arborescens*. Table 1 shows comparisons between 'NCHA1' and two other commercial *hydrangea* cultivars, 'Annabelle' (unpatented) and 'Eco Pink Puff' (unpatented).

TABLE 1

COMPARSION TO COMMERCIAL CULTIVARS

| Characteristic | 'NCHA1' | 'Annabelle' | 'Eco Pink Puff' |
|---|---|---|---|
| Inflorescence corymb diameter | 8 cm to 20 cm | 26 cm to 32 cm | 6 cm to 10 cm |
| Inflorescence corymb height | 5 cm to 12 cm | 22 cm to 26 cm | 2 cm to 6 cm |
| Sterile flowers number per corymb | 600 | 1,650 | 0 to 4 |
| Mature sepal color when fully expanded | Rose to pink (RHS 68D to RHS 68C and RHS N66D to RHS N66C) | Ivory (RHS 155C) | Pale Pink (RHS 69C) |

I claim:

1. A new and distinct cultivar of *Hydrangea* plant as shown and described herein.

* * * * *